(12) United States Patent
Grauwinkel et al.

(10) Patent No.: US 11,850,412 B2
(45) Date of Patent: Dec. 26, 2023

(54) INTRAVASCULAR BLOOD PUMP ROTOR

(71) Applicant: ABIOMED, Inc., Danvers, MA (US)

(72) Inventors: Marius Grauwinkel, Aachen (DE);
Jim-Po Wang, Danvers, MA (US);
Wolfgang Kerkhoffs, Aachen (DE)

(73) Assignee: ABIOMED, INC., Danvers, MA (US)

( * ) Notice: Subject to any disclaimer, the term of this patent is extended or adjusted under 35 U.S.C. 154(b) by 0 days.

(21) Appl. No.: 17/713,695

(22) Filed: Apr. 5, 2022

(65) Prior Publication Data

US 2022/0323742 A1 Oct. 13, 2022

Related U.S. Application Data

(60) Provisional application No. 63/172,393, filed on Apr. 8, 2021.

(51) Int. Cl.
| | |
|---|---|
| *A61M 60/221* | (2021.01) |
| *A61M 60/148* | (2021.01) |
| *A61M 60/824* | (2021.01) |
| *A61M 60/82* | (2021.01) |
| *A61M 60/422* | (2021.01) |
| *F04D 13/02* | (2006.01) |

(52) U.S. Cl.
CPC ........ *A61M 60/221* (2021.01); *A61M 60/148* (2021.01); *A61M 60/422* (2021.01); *A61M 60/82* (2021.01); *A61M 60/824* (2021.01); *F04D 13/027* (2013.01)

(58) Field of Classification Search
CPC .... F04D 13/027; F04D 13/066; F04D 29/181; F04D 29/183; F04D 29/186; A61M 60/422; A61M 60/237; A61M 60/82; A61M 60/804
See application file for complete search history.

(56) References Cited

U.S. PATENT DOCUMENTS

| | | | |
|---|---|---|---|
| 8,870,552 B2 | 10/2014 | Ayre et al. | |
| 2003/0091450 A1* | 5/2003 | Davis | A61M 60/221 417/423.7 |
| 2011/0238172 A1 | 9/2011 | Akdis | |
| 2019/0298902 A1* | 10/2019 | Siess | A61M 60/216 |

* cited by examiner

*Primary Examiner* — Kenneth J Hansen
(74) *Attorney, Agent, or Firm* — MEAGHER EMANUEL LAKS GOLDBERG & LIAO, LLP

(57) ABSTRACT

A blood pump rotor for an intravascular blood pump includes a distal portion having a rotor hub. A distal end of the rotor hub extends beyond a most distal portion of at least one blade formed on the hub. A proximal portion comprises permanent magnets arranged to form a modified Halbach array generating a magnetic field with a first magnetic flux in a proximal direction that is greater than a second magnetic flux in the distal direction. The array is arranged so that: (a) at least one axial magnetized magnet has a most proximal point that is a different distance from said distal end as compared to a most proximal point of at least one circumferential magnetized magnet, (b) at least one axial magnetized magnet has a physical dimension that is different from a corresponding physical dimension of at least one circumferential magnetized magnet, or (c) a combination thereof.

19 Claims, 12 Drawing Sheets

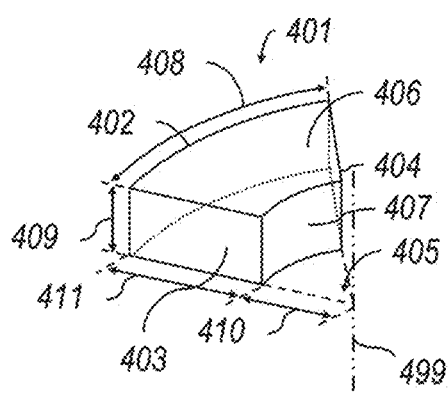
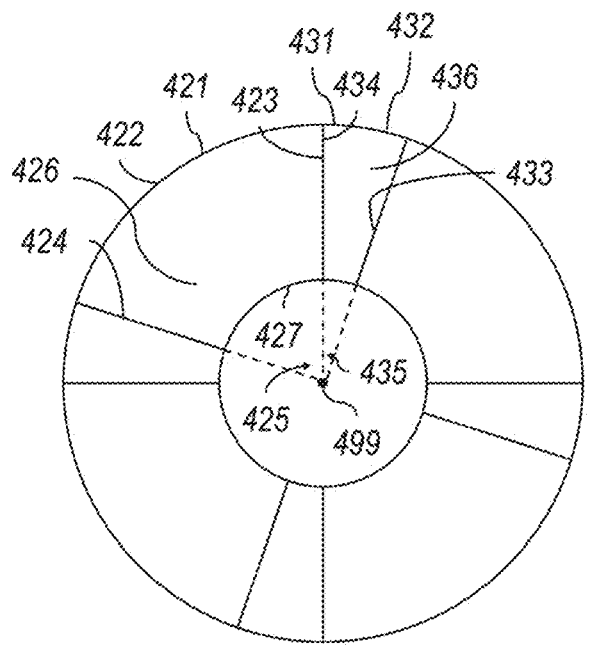
FIG. 4A
FIG. 4B
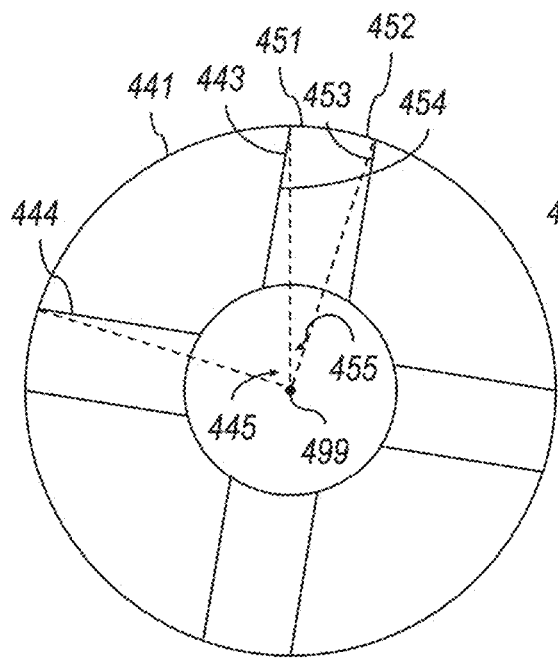
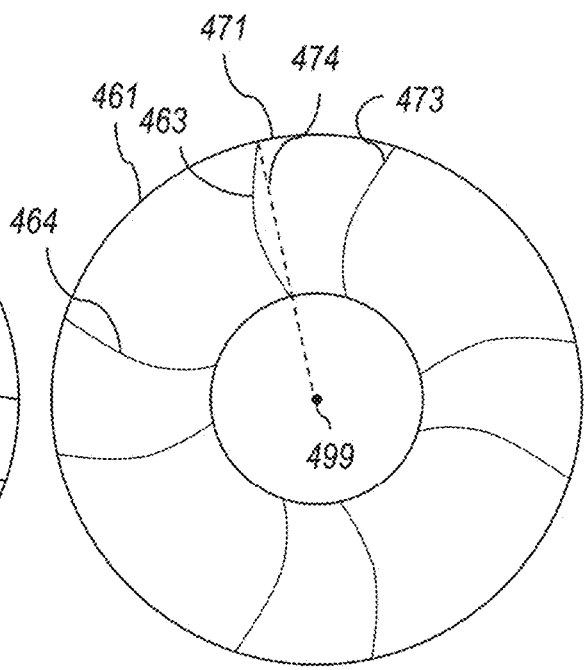
FIG. 4C
FIG. 4D

INTRAVASCULAR BLOOD PUMP ROTOR

CROSS-REFERENCE TO RELATED APPLICATIONS

This application claims priority to U.S. Provisional Application No. 63/172,393, filed Apr. 8, 2021, which is herein incorporated by reference in its entirety.

BACKGROUND

The present disclosure relates to a blood pump, in particular a rotor for an intravascular blood pump for percutaneous insertion into a patient's blood vessel, to support a blood flow in a patient's blood vessel. The blood pump has an improved rotor which allows for increased efficiency and reduction of the outer diameter of the blood pump.

Blood pumps of different types are known, such as axial blood pumps, centrifugal (i.e., radial) blood pumps or mixed-type blood pumps, where the blood flow is caused by both axial and radial forces. Intravascular blood pumps are inserted into a patient's vessel such as the aorta by means of a catheter. A blood pump typically comprises a pump casing having a blood flow inlet and a blood flow outlet connected by a passage. In order to cause a blood flow along the passage from the blood flow inlet to the blood flow outlet, a rotor is rotatably supported within the pump casing, with the rotor being provided with blades for conveying blood.

Blood pumps are typically driven by a drive unit, which can be an electric motor. For instance. US 2011/0238172 A1 discloses extracorporeal blood pumps having an impeller which may be magnetically coupled to an electric motor. The rotor comprises magnets which are disposed adjacent to magnets in the electric motor. Due to attracting forces between the magnets in the impeller and in the motor, rotation of the motor is transmitted to the rotor. In order to reduce the number of rotating parts, it is also known from US 2011/0238172 A1 to utilize a rotating magnetic field, with the drive unit having a plurality of static posts arranged about the axis of rotation, and each post carrying a wire coil winding and acting as a magnetic core. A control unit sequentially supplies a voltage to the coil windings to create the rotating magnetic field. In order to provide a sufficiently strong magnetic coupling, the magnetic forces have to be high enough, which can be achieved by a sufficiently high current supplied to the drive unit or by providing large magnets, which, however, leads to a large overall diameter of the blood pump. However, high energy consumption and heat generation may occur in such drive units.

To increase drive efficiencies, blood pumps typically utilize magnetic yokes, which are generally composed of ferromagnetic iron and are placed on either side of the rotor-stator combination. For instance, U.S. Pat. No. 8,870,552 discloses a rotary blood pump with a rotor sandwiched between front and back windings, where the pump uses a conical ferromagnetic iron yoke on the outside of a front winding and an annular iron ferromagnetic yoke on the outside of a back winding

BRIEF SUMMARY

It is therefore an object of the present disclosure to provide a blood pump, preferably an intravascular blood pump or transvalvular blood pump, having a magnetic coupling between the drive unit and the impeller, wherein the blood pump has a compact design, in particular a sufficiently small outer diameter to allow the blood pump to be inserted transvascularly, transvenously, transarterially or transvalvularly. It is further an object of the present disclosure to reduce heat and energy consumption of the blood pump, which is particularly useful for long-term applications in which the blood pump can be battery-powered to provide mobility for the patient, without the need for any magnetic yoke.

This object is achieved according to the present disclosure by a blood pump rotor having the features of the independent claims. Preferred embodiments and further developments of the present disclosure are specified in the claims dependent thereon.

According to the present disclosure, the blood pump rotor is configured to rotate around an axis of rotation. It comprises a distal portion and a proximal portion. The distal portion includes a rotor hub, which tapers in a distal direction. The rotor hub has at least one blade extending outward from the rotor hub. Further, a distal end of said rotor hub extends distally beyond a most distal portion of the at least one blade. The proximal portion, which is connected to the distal portion, has permanent magnets arranged so as to form a modified Halbach array generating a magnetic field having a magnetic flux in a proximal direction that is greater than a magnetic flux in a distal direction, said first magnetic flux being greater than said second magnetic flux.

The modified Halbach array utilizes an alternating arrangement of axial magnetized magnets and circumferential magnetized magnets, where the Halbach array may be modified in one of three ways.

In a first aspect, at least one axial magnetized magnet has a most proximal surface that is a different distance from the distal end compared to a most proximal surface of at least one circumferential magnetized magnet. In preferred embodiments of the first aspect, a most proximal point on the surface of each circumferential magnetized magnet is closer to the distal end, generally in a range of between 1 mm and 7 mm closer, than a most proximal point on the surface of each axial magnetized magnet. Said differently, the axial magnetized magnets are configured to be closer to an electric drive unit of the blood pump than the circumferentially magnetized magnets. Further, while the proximal surfaces may be orthogonal to the axis of rotation, in some embodiments the proximal surfaces of the magnets may be shaped, and therefore the proximal surfaces may be non-orthogonal to the axis of rotation, and in some instances at least two of the circumferentially magnetized magnets may not be coplanar.

In a non-modified Halbach arrangement, the physical dimensions of each magnet in the array are identical, and only the direction of magnetization differs. In a second aspect of the modified Halbach array, at least one axial magnetized magnet has a physical dimension that is different from a corresponding physical dimension of at least one circumferential magnetized magnet. For instance, in some embodiments, each permanent magnet comprises two side surfaces extending radially away from the axis of rotation, and the two side surfaces for each magnet form either (a) two parallel flat surfaces, (b) two non-parallel flat surfaces, or (c) a concave curved surface and a convex curved surface.

At any given axial distance along the magnet, the outer surface of each magnet in a radial direction will generally form an arc (i.e., the outer surface will have a cross-sectional shape forming an arc of a circle about the axis of rotation), which may differ in length between magnets. In some embodiments, an angle subtended by each arc from the axis of rotation is between 1° and 89°, and two different magnets may have different subtended angles. In some embodiments, at least one of the angles is greater than 45 degrees, and/or at least one of the angles is less than 45 degrees. Additionally, or alternatively, one or more of the magnets may be longer, in an axial direction, than one or more other magnets in the array.

In a third aspect, the first and second aspects are combined, that is, at least one axial magnetized magnet has a most proximal surface that is a different distance from the distal end compared to a most proximal surface of at least one circumferential magnetized magnet and at least one axial magnetized magnet has a physical dimension that is different from a corresponding physical dimension of at least one circumferential magnetized magnet.

These blood pump rotors can be incorporated into intravascular blood pumps, which may be an axial blood pump or a diagonal blood pump, which pumps partly axially and partly radially, (the diameter of pure centrifugal blood pumps is usually too large for intravascular applications). Typically, the blood pumps will include a pump casing having a blood flow inlet and a blood flow outlet, the intravascular blood pump rotor, and an electric drive unit (which may comprise a 2, -4-, or 6-pole stator) that is capable of magnetically interacting with said intravascular blood pump rotor. In some embodiments, each circumferential magnetized magnet is further from a distal end of the electric drive unit than each axial magnetized magnet.

The electric drive unit creates a rotating electromagnetic field allows for simplification of the mechanics of the blood pump by reducing the number of moving parts compared to a common electric motor. This also reduces wear, because no contact bearing for an electric motor is necessary. The magnetic coupling between the drive unit and the impeller not only causes rotation of the impeller but also permits correct alignment of the impeller.

The distal surface of the drive unit may be flat or orthogonal to the axis of rotation, or may be oblique or inclined. The distal surface of drive unit be substantially triangular or trapezoidal in cross-section along a plane including the axis of rotation. In the assembled state, the distal surface of the drive unit may form a conical surface or substantially conical surface, e.g., a surface having facets but forming approximately a conical surface. Generally, the shape of the formed surface can be convex. Illustratively speaking, the portions of the drive unit may be put together like pie slices to form a circular arrangement having a conical top surface.

The magnets of the rotor may have or may form a conical or substantially conical recess substantially corresponding in size and shape to the conical surface formed by the distal surface of the drive unit. Generally, the magnets may form a concave surface facing the convex surface formed by the drive unit improve the magnetic coupling. In another embodiment, the arrangement of concave and convex surfaces may be vice versa, i.e., the distal surface of the drive unit may form a conical recess while the rotor magnets forms a convex conical surface.

The distal surface of the drive unit and the proximal surfaces rotor will be separated by a gap. The shape and dimension of the gap between the rotor and the drive unit may contribute to hydrodynamic bearing capabilities.

The Halbach array will generally be provided as a plurality of magnets, such as four or more, and preferably at least eight magnets. Various embodiments utilize six magnets, eight, ten, twelve, fourteen, sixteen, or twenty four magnets, that are arranged in the impeller about the axis of rotation. Preferably, an even number of magnets is provided, more preferably a number that is a multiple of the number of poles of the stator, is advantageous to avoid or minimize dead zones. The magnets may be arranged with substantially no gaps between the individual magnets in order to increase the amount of magnetic material. However, it has been found that the efficiency of the magnetic coupling does not decrease if the magnets are separated by gaps, in particular radially extending gaps. This is because of the characteristics of the magnetic field and the gap between the drive unit and the impeller. If the magnets in the rotor are close to each other, the innermost magnetic field lines, which extend in an arch from one magnet (north) to an adjacent magnet (south), do not extend beyond the gap between the drive unit and the impeller and, thus, do not reach the drive unit, i.e., they do not contribute to the drive of the impeller. Therefore, there is no loss in efficiency if a gap is provided between the magnets in the impeller. The size of gap between the magnets in the impeller that can be provided without loss of efficiency of the drive is dependent on the size of the gap between the impeller and the drive unit as a skilled person can calculate. The gaps between the impeller magnets can then be used, e.g., as wash out channels.

In order to enhance a wash-out flow through the gap between the rotor and the drive unit, a secondary set of blades may be provided in the rotor. In particular, secondary blades may be provided on the side of the magnet or magnets that faces the drive unit, i.e., in the gap between the rotor and the drive unit. In preferred embodiments, one or more of the circumferential magnetized magnets may include one or more secondary blades connected to or formed onto a proximal surface of the magnet, extending axially away from the proximal surface in a proximal direction. In embodiments where the proximal surfaces of the axial and circumferential magnetized magnets are at different distances from the drive unit, the secondary blades preferably do not extend beyond the most proximal portion of the axial magnetized magnets.

The wash-out flow may additionally or alternatively be increased by channels that are recessed in the surface of the magnet that faces the drive unit. The channels may extend e.g. radially or helically.

BRIEF DESCRIPTION OF DRAWINGS

FIG. 4A is a simplified illustration of a magnet in an embodiment of a modified Halbach array.

FIGS. 4B-4F are cross-sectional illustrations of alternative configurations of magnets for embodiments of modified Halbach arrays.

DETAILED DESCRIPTION

Figure 1:
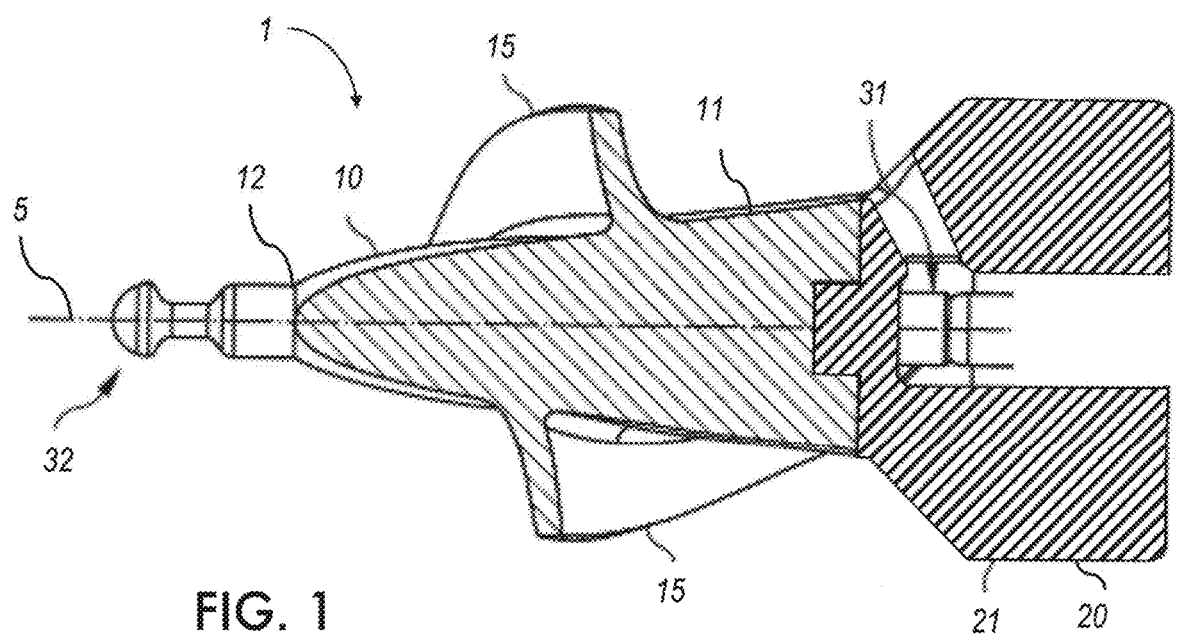
FIG. 1 is an illustration of an embodiment of a blood pump rotor and drive unit.

Referring to FIG. 1A, a cross-sectional view of an intravascular blood pump rotor is illustrated. The rotor 1 has a distal portion 10 and a proximal portion 20. Proximal portion 20 is connected to the proximal end of distal portion 10.

The rotor 1 (which may sometimes be referred to as an impeller) is configured to rotate about the axis of rotation 5 by means of a first bearing 31 and a second bearing 32. Both bearings 31, 32 are contact-type bearings in this embodiment. At least one of the bearings 31, 32 could be a non-contact-type bearing, however, such as a magnetic or hydrodynamic bearing. The first bearing 31 is a pivot bearing having spherical bearing surfaces that allow for rotational movement as well as pivoting movement to some degree.

The distal portion 10 includes a rotor hub 11 tapering in a distal direction towards the most distal end 12 of the rotor hub 11. The second bearing 32 is typically connected to rotor 1 at the most distal end 12 of rotor hub 11. At least one blade 15 is provided on the rotor 1 for conveying blood once the rotor 1 rotates. Any blade 15 is generally connected to rotor hub 11. Distal end 12 of the rotor hub 11 extends distally beyond a most distal portion of blade 15. and The proximal portion 20 contains permanent magnets 21 arranged so as to form a modified Halbach array.

Figure 2A:
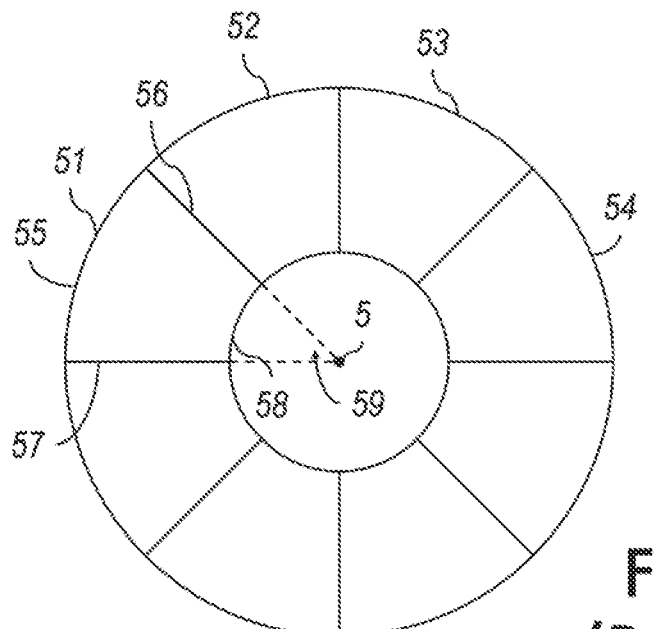
FIG. 2A is an illustration of an arrangement of magnets forming a cylindrical Halbach array.

Referring briefly to FIG. 2A, a standard cylindrical Halbach array is typically composed of a plurality of magnets 51, 52, 53, 54. Each magnet is generally identical, save for the magnetization direction. In standard cylindrical Halbach arrays, the proximal surfaces of all magnets are generally aligned, and each magnet has an outer surface 55, an inner surface 58 closest to the axis of rotation 5, and two side surfaces 56, 57 that extend radially away from the axis of rotation 5. The outer surface 55 of each magnet generally has a cross-sectional shape forming an arc of a circle about the axis of rotation 5, and there is an angle 59 subtended by each arc from the axis of rotation 5.

Figure 2B:
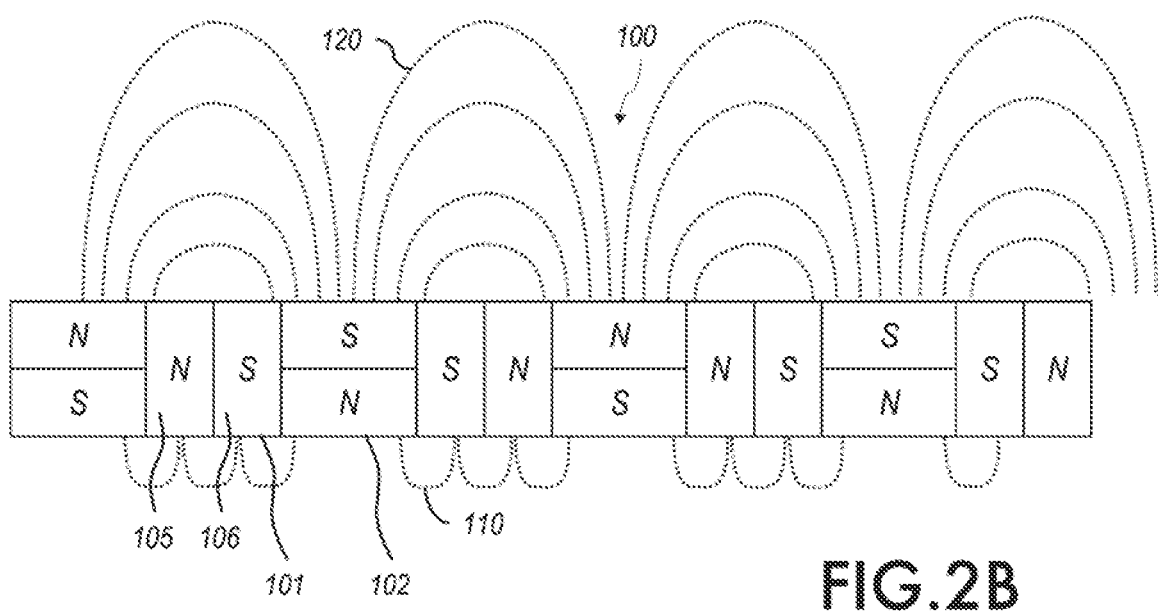
FIG. 2B is an illustration of one embodiment for the magnetization of magnets resulting in a Halbach array, and resulting magnetic fluxes.

Referring to FIG. 2B, traditional Halbach arrays 100 comprise an alternating arrangement of circumferential magnetized magnets 101 (e.g., the two poles 105, 106 are separated in a substantially circumferential direction) and axial magnetized magnets 102 (e.g., the two poles are separated in a substantially axial direction). The proximal surface 103 and distal surface 104 of each magnet are substantially identical (in shape and axial/radial position) to the proximal and distal surfaces of the other magnets in the array. The proximal surfaces 103 of all magnets are typically substantially aligned, such that no part of any magnet in the array extends beyond the respective part of another magnet in the array. In this arrangement, a Halbach array will exhibit a relatively strong magnetic flux on one side and a relatively weak magnetic flux on the opposite side.

Rather than having the strong/weak magnetic fluxes be generated in a radial direction as is typically done, the modified Halbach arrays of the present disclosure generate these strong/weak magnetic fluxes in an axial direction. That is, the modified Halbach array in the presently disclosed rotor generates a magnetic field having a first magnetic flux 120 in a proximal direction and a second magnetic flux 110 in a distal direction. The first magnetic flux 120 is greater than the second magnetic flux 110.

Additionally, the traditional cylindrical Halbach arrays shown in FIGS. 2A and 2B are modified for use in the present disclosure in one of three ways.

First Modification Approach

The first modification approach is to modify the arrangement of magnets in an axial direction. This technique involves creating differences in positioning and/or orientation of proximal surfaces of axial and circumferential magnetized magnets in the Halbach array.

Figure 3A:
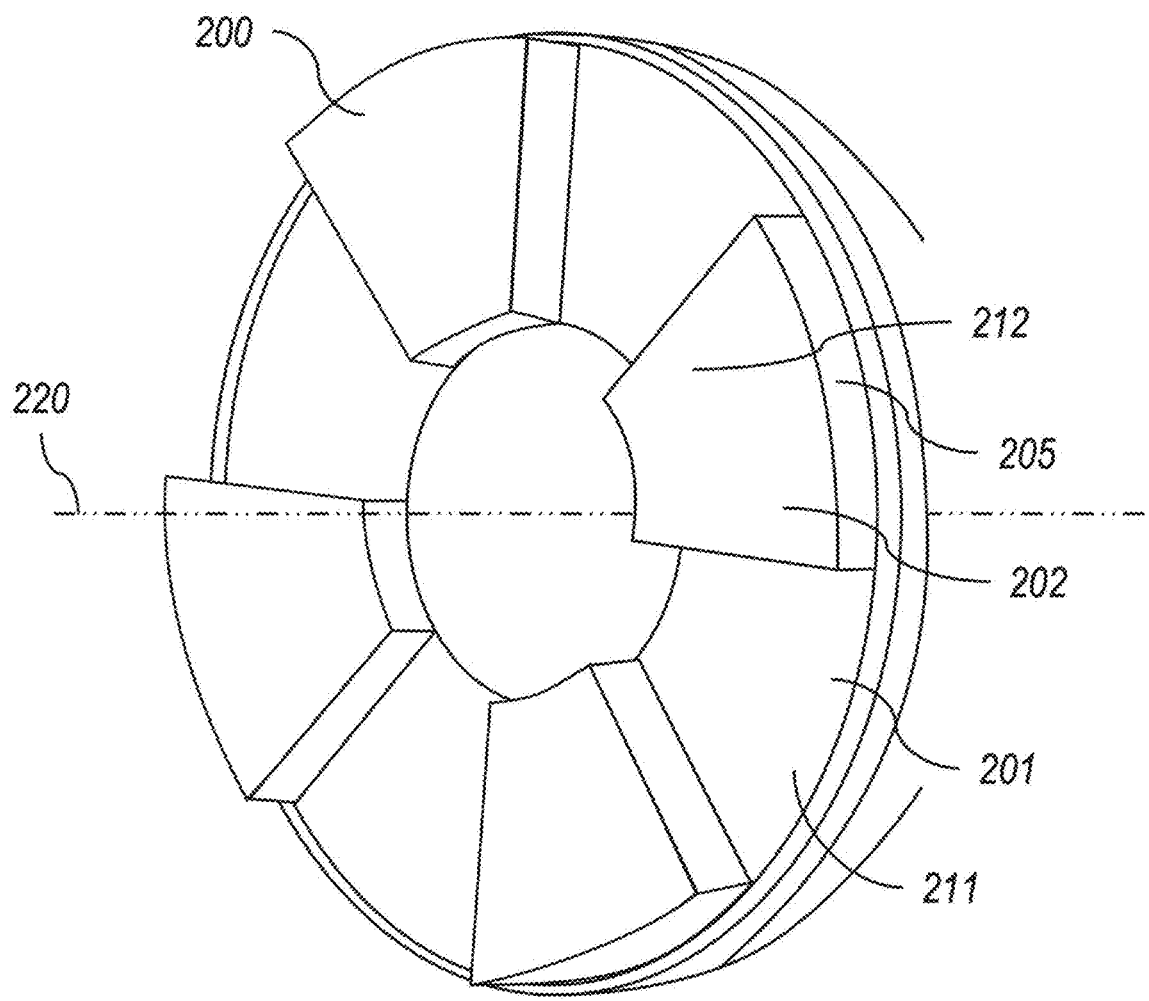
FIG. 3A is a projection view of an embodiment of a modified Halbach array, focusing on an end portion of the array.

In particular, as shown in FIG. 3A, a Halbach array 200 of the present disclosure will contain alternating circumferential magnetized magnets 201 and axial magnetized magnets 202 in a cylindrical arrangement around an axis of rotation 220. The proximal surface 212 of at least one axial magnetized magnet 202 is a different distance along an axial direction from the proximal surface 211 of at least one circumferential magnetized magnet 201. As seen in FIG. 3A, a portion of the outer surface 205 of the axial magnetized magnet may extend proximally beyond the proximal surface 211 of at least one circumferential magnetized magnet 201.

Various embodiments of this can be illustrated with reference to FIGS. 3B, 3C, and 3D. These two figures are simplified illustrations of the most proximal portions of the magnets in embodiments of modified Halbach arrays according to the present disclosure.

Figure 3B:
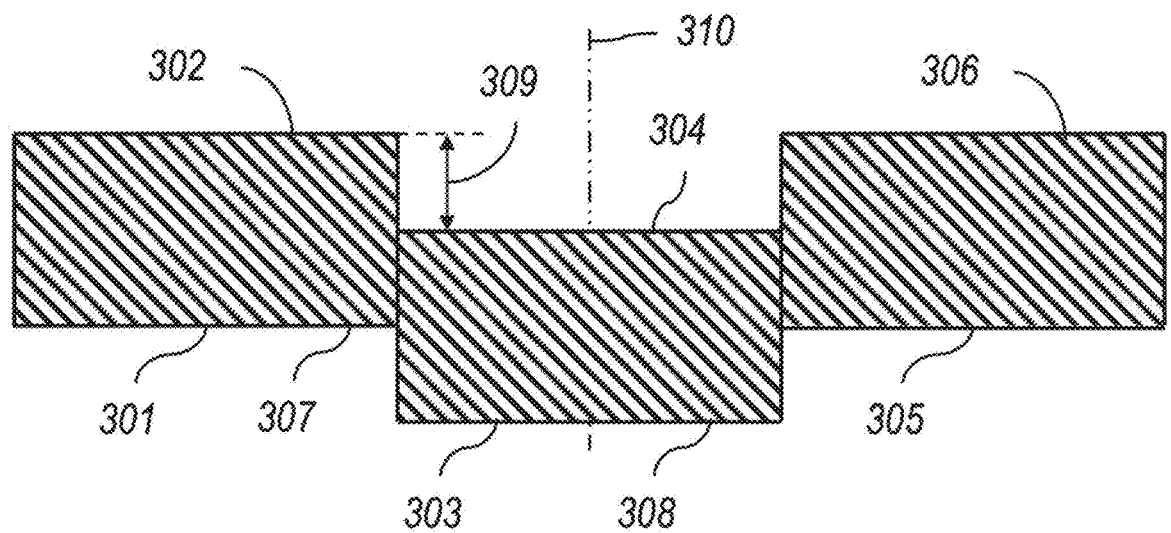
FIG. 3B is a simplified illustration of a side view of one embodiment of a modified Halbach array.

In particular, FIG. 3B provides a simplified illustration showing a side view of the proximal ends of two axial magnetized magnets 301, 305, and one circumferential magnetized magnet 303 where the most proximal surface of each magnet is orthogonal to the axis of rotation 310. Note that as the proximal surfaces of each magnet in this embodiment are orthogonal to the axis of rotation, any point or portion of the proximal surface would qualify as the most proximal point or portion of that magnet.

As the most proximal surfaces 302, 304, 305 in the illustration are flat, any point can be considered the most proximal portion, and thus, the difference 309 in axial locations of the most proximal portions of an axial magnetized magnet 301 and a circumferential magnetized magnet 303 can be readily determined.

If the physical dimensions of the magnets are identical, this difference in axial positioning can be created by simply offsetting the axial positioning of the axial magnetized magnets as compared to the circumferential magnetized magnets. This is illustrated in FIG. 3B, where the most distal surface 307 of magnet 301 is offset axially from the most distal surface 308 of magnet 303.

FIG. 3B provides a similar illustration, but in this embodiment, the most proximal surfaces 312, 314, 316 of the axial magnetized magnets 313 and circumferential magnetized magnets 311, 315 are shaped and not necessarily orthogonal to the axis of rotation. In this example, the shaped surfaces are shown as simple angled flat surfaces, but skilled artisans will recognize that curves or complex shapes can easily be incorporated as appropriate. An axis of rotation 320 and a direction of rotation 321 of the rotor is also provided for reference.

As seen in FIG. 3B, the most proximal point or portion 318 of the axial magnetized magnet 313 (here, the trailing edge of the magnet) is identified along with the most proximal portion 317 of the circumferential magnetized magnet 311. In preferred embodiments, the most proximal point or portion 317 of the circumferential magnetized magnet is in the same relative position on the proximal surface as the most proximal point or portion 318 of the axial magnetized magnet. For example, if the most proximal point or portion 318 of the axial magnetized magnet is on the trailing edge (according to the direction of rotation 321 of the rotor) of the outermost surface of the axial magnetized magnet, then the most proximal point or portion 317 of the circumferential magnetized magnet is preferably on the trailing edge of the outermost surface of the circumferential magnetized magnet. The difference 319 in axial location of the most proximal points or portions 317, 318 can then be determined. Similar to the embodiment in FIG. 3A, if the physical dimensions of the magnets are identical, this difference in axial positioning can be located by simply offsetting the axial positioning of the axial magnetized magnets as compared to the circumferential magnetized magnets.

In preferred embodiments, the difference in axial position is between 1 mm and 7 mm. Said differently, the most proximal portion of the circumferential magnetized magnet is preferably between 1 mm and 7 mm closer to the distal end of the rotor than the most proximal portion of the axial magnetized magnet. In some embodiments, this difference is at least 0.5 mm, 1 mm, 2 mm, 3 mm, 4 mm, or 5 mm, and no more than 10 mm, 8 mm, 7 mm, 6 mm, 5 mm, 4 mm, 3 mm, or 2 mm, including all possible combinations and subranges thereof.

In preferred embodiments, the most proximal portion of each circumferential magnetized magnet is an identical distance from the distal end of the rotor, and the most proximal portion of each axial magnetized magnet is an identical distance from the distal end of the rotor. In some embodiments, however, that may not be desirable, and thus other combinations are envisioned.

For example, in some embodiments, the most proximal surfaces of the circumferential magnetized magnets are not all equally distant from the distal end of the rotor, while the most proximal surfaces of all axial magnetized magnets are. In other embodiments, the reverse is true, the most proximal surfaces of all circumferential magnetized magnets are at equal distances from the distal end of the rotor, while at least some of the most proximal surfaces of the axial magnetized magnets are not And in still other embodiments, the most proximal surfaces of the circumferential magnetized magnets are not all equally distant from the distal end of the rotor, and the most proximal surfaces of all axial magnetized magnets are also not equally distant from the distal end of the rotor.

Additionally, in some embodiments, at least two of the most proximal surfaces of the circumferential magnetized magnets are not coplanar. This may result from, for example, magnets having proximal surfaces that are angled or curved in a circumferential direction and/or a radial direction. For instance, as seen in FIG. 3B, the proximal surfaces 312, 316 of circumferential magnetized magnets 311, 315 (which have identical physical dimensions) are angled in a circumferential direction, and thus are not coplanar. Alternatively, it is clear that when the proximal surfaces of the magnets form a conical or substantially conical surface, the proximal surfaces would not be coplanar.

Figure 3C:
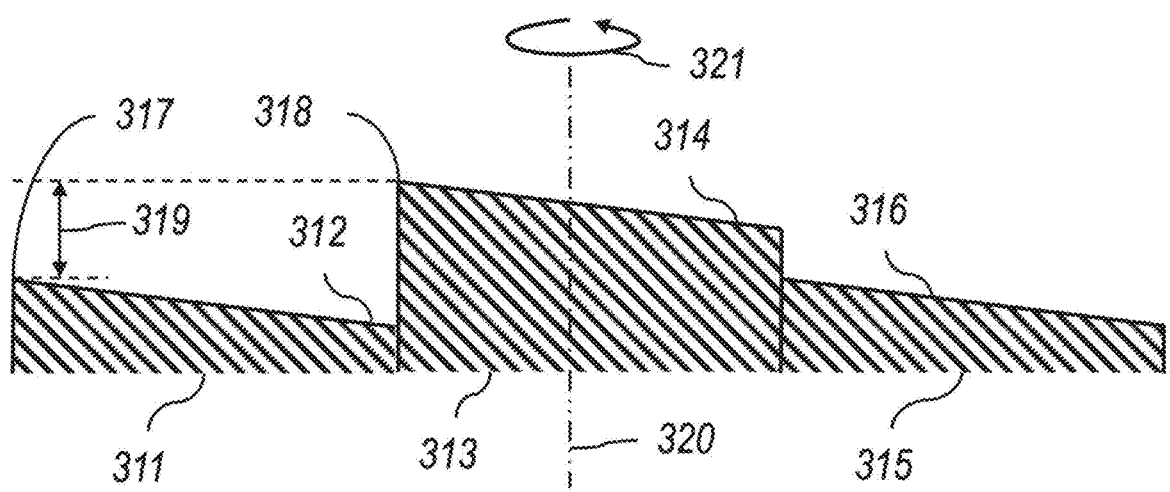
FIG. 3C is a simplified illustration of a side view of an alternative embodiment of a modified Halbach array.
Figure 3D:
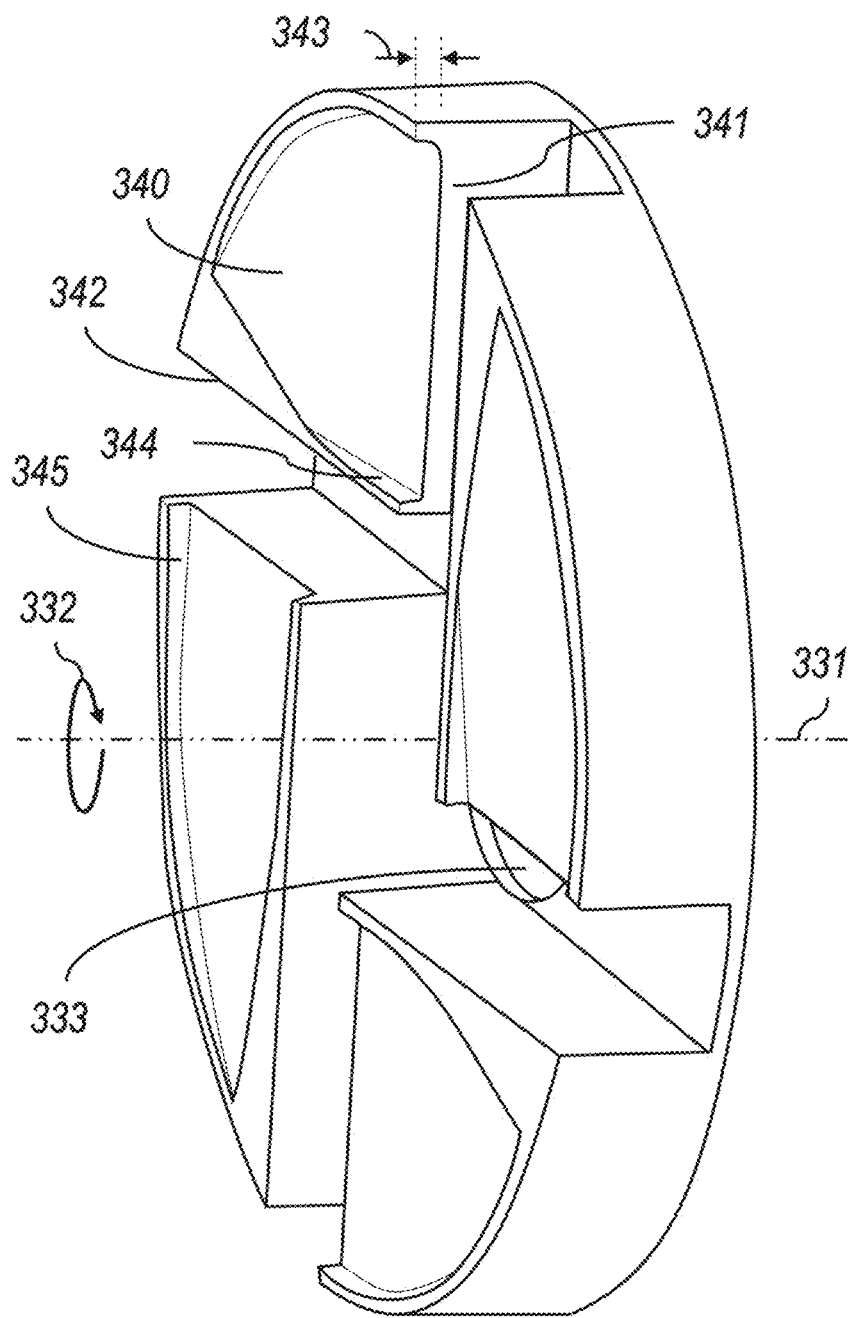
FIG. 3D is a projection view of another embodiment of a modified Halbach array, focusing on an end portion of the array

In FIG. 3C, an embodiment can be seen that combines some of the features seen in FIGS. 3A and 3B Specifically, as seen in FIG. 3D, magnets are arranged to rotate in a clockwise direction 332 around a central axis 331. An inner surface 333 defines a central opening having a first diameter, and an outer surface 334 defines the outer edge of the magnet array, having a second diameter greater than the first diameter. In this figure, several first portions 335 alternate with several second portions 340. Each first portion is substantially flat and orthogonal to the axis of rotation 331. Each second portion 340 is offset axially from the first portion 335. The second portion has a leading surface 344 and a trailing surface 345.

A first subportion 343 of the most proximal surface of each second portion 340 may be parallel to the first portion. That is, in some embodiments, there may be a flat runout zone where the pressure can be distributed over the surface and the fluid can flow off the second portion 340.

A second subportion 342 of the most proximal surface of each section portion 340 may be contoured in some embodiments, the contour is a rising contour in the counterclockwise direction (opposite the direction of rotation). The contour may taper a distance 348 from a most distal point 349 (such as a point near the leading surface 344) to a most proximal point 350 (such as a point at or near the trailing surface 345 or the first subportion 343) That is, one part (e.g., ref. 349) of the most proximal surface of the second portion 340 may be closer to the first portion 335 in an axial direction than a second part (e.g., ref. 350) of the most proximal surface of the second portion by a distance 348.

In some embodiments, no portion of the second subportion 342 is coplanar with the first subportion 343. In some embodiments, the second subportion 342 comprises a curved surface (e.g., a concave or convex surface). In some embodiments, the second subportion 342 comprises a substantially flat surface at a fixed angle relative to the first portion 340.

In some embodiments, the second subportion 340 may include sidewalls, such as a trailing sidewall 346 at the trailing surface 345, or an outer sidewall 347 at the outer surface 334 of the array. These sidewalls may be used to control the flow of blood, reducing flow in a radial direction, etc.

Further, a skilled artisan will recognize that although the magnets illustrated in the figures are shown as having sharp corners, the edges may be fully or partially beveled, chamfered, rounded, etc.

Second Modification Approach

The second modification approach is to configure a physical dimension of at least one axial magnetized magnet to be different from the corresponding physical dimension of at least one circumferential magnetized magnet. That is, rather than all magnets being generally identical except for magnetization direction, the physical dimensions are tweaked such that the axial magnetized magnets are physically different form the circumferential magnetized magnets.

Referring to FIG. 4A, an illustration of an individual magnet 401 in a modified Halbach array is provided. For each magnet 401, there is an outer surface 402, an inner surface 407, and side surfaces 403, 404 extending radially outward away from the axis of rotation 499. Each magnet also has a proximal surface 406.

In preferred embodiments, each permanent magnet has an outer surface 402 with a cross-sectional shape forming an arc of a circle about said axis of rotation 499. The physical dimensions of the arcs are such that the angle 405 subtended by each arc from the axis of rotation 499 is most preferably between 1° and 89°. In some embodiments, the angle is at least 1°, 5°, 10°, 15° or 20°, and no more than 89°, 80°, 70°, 60°, 50°, or 40° including all possible combinations and subranges thereof. For example, in some embodiments, the angle is between 5° and 70°, between 10° and 80°, or between 20° and 70°.

In some embodiments, when the magnets are arranged in a modified Halbach array, the angle subtended by the arc of the outer surface of a first magnet in the array is different from the angle subtended by the arc of the outer surface of a second magnet in the array. In some embodiments, at least one of the angles is greater than a threshold value, and at least one of the angles is less than the threshold value. The threshold value is equal to 360°/n, where n is the number of magnets in the array. So for a Halbach array comprised of 8 magnets, the threshold value is 45°, for 16 magnets the threshold value is 22.5°, and for 24 magnets the threshold value is 15°. In some embodiments, all axial magnetized magnets have different angles subtended by their arcs than all circumferential magnetized magnets. In some embodiments, all axial magnetized magnets have larger angles subtended by their arcs than all circumferential magnetized magnets. In some embodiments, all axial magnetized magnets have smaller angles subtended by their arcs than all circumferential magnetized magnets.

In some embodiments, the angle for the circumferential magnetized magnets or the axial magnetized magnets (but not both) is less than 40°. In some embodiments, the angle is less than 30°. In some embodiments, the angle is less than 20°. In some embodiments, the angle is less than 10°.

The outer surface 402 that forms an arc also has a maximum arc length 408 (i.e., the longest arc length of an outer surface that can be formed by a plane orthogonal to the axis of rotation) that can vary from magnet to magnet. In preferred embodiments, the arc length of each magnet in the array is between 1 mm and 5 mm. In some embodiments, the arc length of each magnet in the array is between 1 mm and 4 mm or between 1 mm and 3 mm. In some embodiments, the arc length of each magnet in the array is between 2 and 3 mm. In the most preferred embodiments using the second technique, the maximum arc length of at least one axial magnetized magnet is different from the maximum arc length of at least one circumferential magnetized magnet.

The proximal surface 406 of each magnet will have a surface area. In preferred embodiments, the surface area of at least one axial magnetized magnet is different from the surface area of at least one circumferential magnetized magnet.

In the most preferred embodiments, each axial magnetized magnet either (a) has a larger maximum arc length and a larger surface area than each circumferential magnetized magnet, or (b) has a smaller maximum arc length and a smaller surface area than each circumferential magnetized magnet.

Each magnet 401 also has an axial length 409 (i.e., the distance between the most proximal point of the magnet and the most distal point of the magnet). In some embodiments, the axial length of at least one axial magnetized magnet is different from the axial length of at least one circumferential magnetized magnet.

When arranged in the modified Halbach array, the array will have a substantially cylindrical cross-section. The maximum outer diameter of the modified Halbach array is generally less than 7 mm, such as <6.75 mm, or <6.5 mm. In this configuration, the inner surfaces of each magnet will form an opening that may extend at least partially through the modified Halbach array, and preferably extends through the entire modified Halbach array. The opening will generally have a diameter of between 0.5 mm and 2 mm. Thus, the inner surface 407 of each magnet is typically a distance 410 from the axis of rotation 499 that is between 0.25 mm and 1 mm.

Additionally, each side surface 403, 404 will have a length that extends between an inner surface and an outer surface. In FIG. 4A, side surface 403 is shown as having a length 411 that is measured from the inner surface 407 to the outer surface 402. It will be recognized that this length may or may not be the same as the radial distance of the outer surface from the inner surface; for example, if the side surface is curved, the length 411 would be greater than the radial distance between the inner and outer surface. In general, each side surface of each magnet will have a length between 1 mm and 5 mm, such as between 1 mm and 4 mm, or 2 mm and 4 mm.

Skilled artisans will recognize that some all of these differences in physical dimensions may be combined in a single array. For example, in some embodiments, both the arc length and axial length may differ between axial magnetized magnets and circumferential magnetized magnets.

Referring to FIGS. 4B-4E, various alternative physical configurations of magnets in modified Halbach arrays are illustrated.

In FIG. 4B, the modified Halbach array is shown as having an alternating arrangement of circumferential magnetized magnets 421 and axial magnetized magnets 431 configured around an axis of rotation 499, where each magnet 421, 431 in the array has two non-parallel flat side surfaces 423, 424, 433, 434 extending radially outward away from the axis of rotation 499, from an inner surface 427 of each magnet. Each magnet has an outer surface 422, 432, and a most proximal surface 426, 436. The outer surfaces 422, 432 have cross-sectional shapes forming an arc of a circle about said axis of rotation 499, with an angle 405, 415 subtended by each arc from the axis of rotation 499. In preferred embodiments, each side surface is configured to be substantially normal to the outer surface, such that an imaginary plane extending along the a side surface of any given magnet in an array would intersect the angle of rotation.

FIG. 4B is illustrated as having circumferential magnetized magnets 421 that have a greater angle subtended by the arc and/or greater arc length than the axial magnetized magnets 431. However, a skilled artisan will recognize that the opposite could also be true that the axial magnetized magnets could have greater angles subtended by their arcs and/or greater arc lengths than the circumferential magnetized magnets.

In preferred embodiments, each side surface will not be configured to be substantially normal to the outer surface; an imaginary plane extending along each flat side surface of a given magnet would not intersect the angle of rotation.

In FIG. 4C, the modified Halbach array is shown as having an alternative arrangement of circumferential magnetized magnets 441 and axial magnetized magnets 451 configured around an axis of rotation 499, but here the axial magnetized magnets 451 have parallel flat side surfaces 453, 454, while the circumferential magnetized magnet 441 have non-parallel flat side surfaces 443, 444. A skilled artisan will recognize that the opposite could also be true—that the axial magnetized magnets could have non-parallel flat side surfaces, while the circumferential magnetized magnets have parallel flat side surfaces.

The modified Halbach array has angles 445, 455 subtended by the arcs of the outer surfaces 442, 442 by the axis of rotation 499. It should be recognized that it is possible for, e.g., angle 405 (from FIG. 4B) and angle 445 (from FIG. 4C) to be identical, while the lengths of the side surfaces may be quite different.

In FIG. 4), the modified Halbach array is shown as having an alternating arrangement of circumferential magnetized magnets 461 and axial magnetized magnets 471 configured around an axis of rotation 499, but here each magnet 461, 471 have two non-flat side surfaces 463, 464, 473, 474. In particular, each magnet has a concave curved surface 463, 473 and a convex curved surface 464, 474.

Figure 4E:
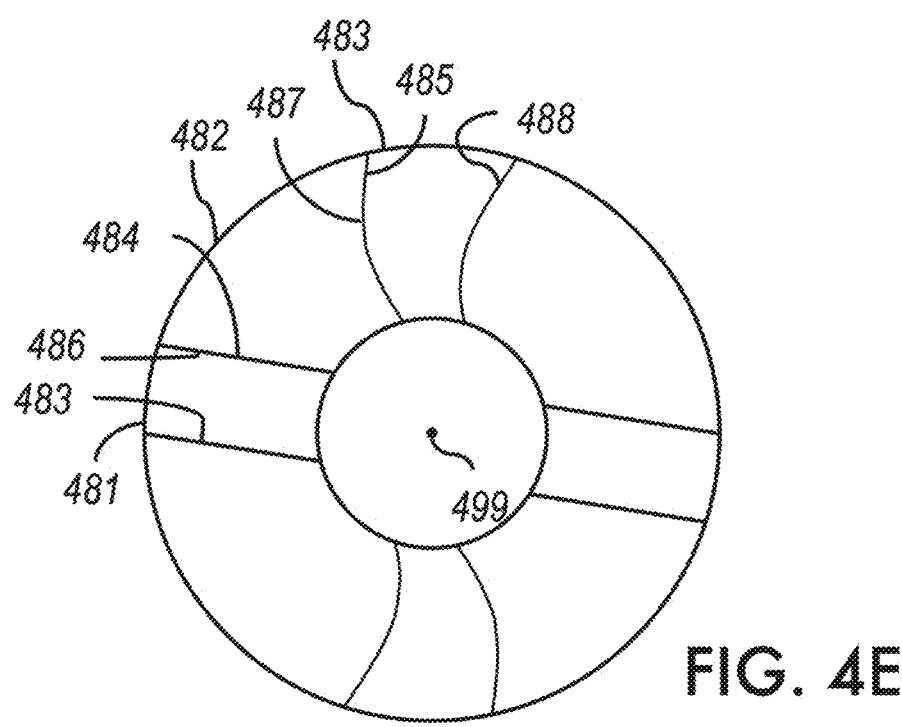

Skilled artisans will recognize that these variations may be combined in various embodiments. For example, as seen in FIG. 4E, the modified Halbach array is shown as having an alternating arrangement of circumferential magnetized magnets 482 and axial magnetized magnets 481, 483. However, a first magnet 481 has two parallel flat side surfaces 483, 486. A second magnet 482 has one flat side surface 484 that is not normal to the outer surface of the magnet (that is, an imaginary plane extending along the flat side surface would not intersect the axis of rotation). The second magnet 482 also has a concave curved surface 487. A third magnet 483 has a concave curved surface 488 and a convex curved surface 485.

Figure 4F:
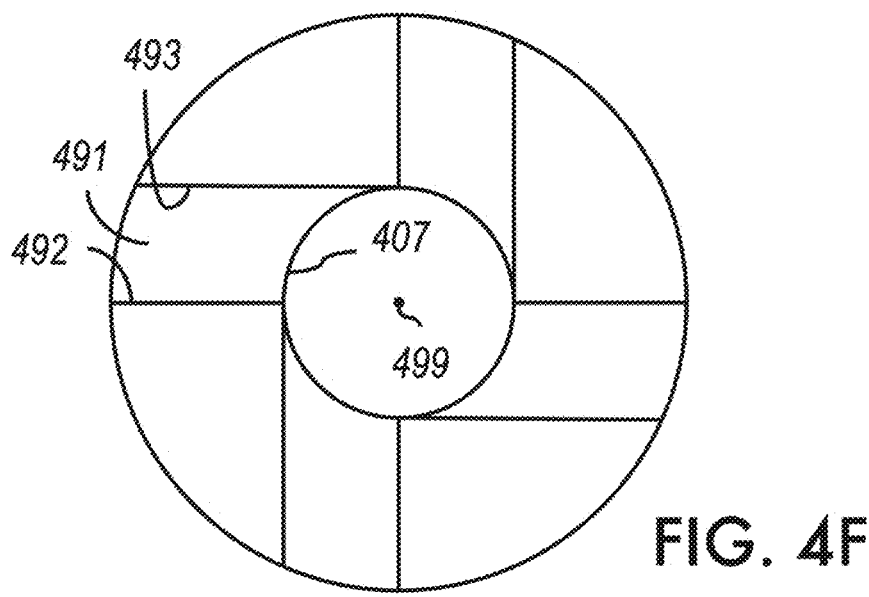

In FIG. 4F, another arrangement is seen. Here, while all magnets have parallel flat sides, the sides are not centered as seen in FIG. 4C. Rather, the plane defined by one side 492 of a first magnet 491 is configured to intersect the axis of rotation 499, while the plane defined by the other side 493 of the first magnet 491 is configured to tangentially intersect the inner surface 407 of the magnet.

Third Modification Approach

The third modification approach combines the first and second modification approaches.

That is, in addition to manipulating the axial positioning of the proximal surfaces as accomplished by the first modification technique, it also includes adjusting physical dimensions of the magnets as well.

Figure 5A:
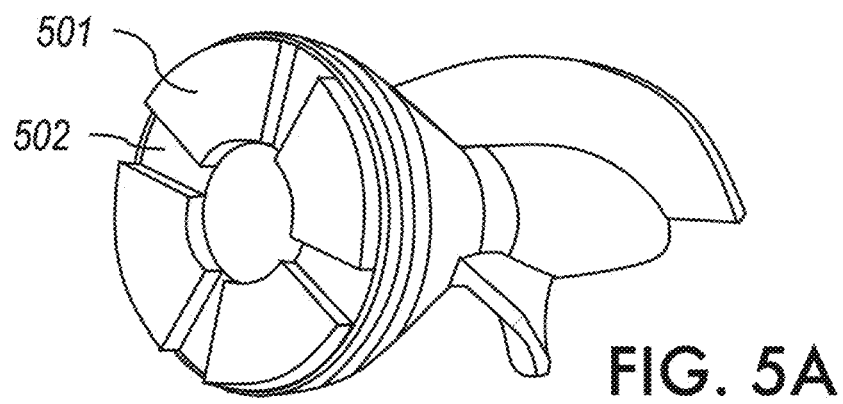
FIGS. 5A-5C are projects of alternate embodiments of a modified Halbach array.

For example, FIG. 5A shows an arrangement of magnets where the proximal surface of each axial magnetized magnet 501 is located further along the axis of rotation (towards the proximal end of the rotor) than the proximal surface of each circumferential magnetized magnet 502, and the outer surface of each axial magnetized magnet has an arc length greater than the arc length of the outer surface of each circumferential magnetized magnet. Each magnet has two non-parallel flat side surfaces.

Figure 5B:
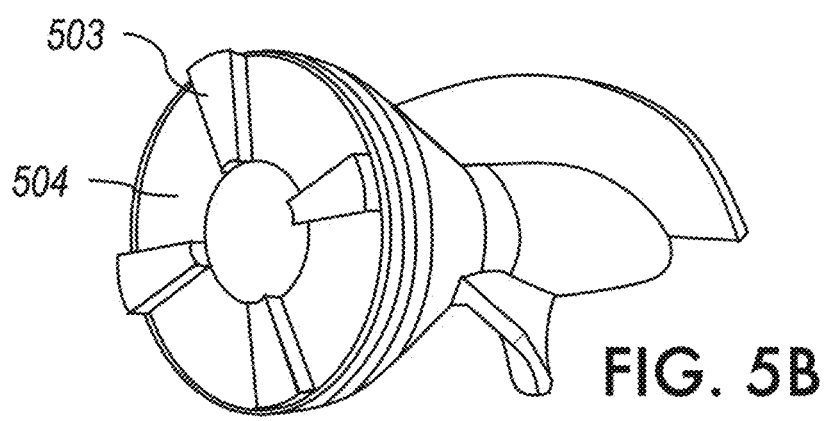

In FIG. 5B, the proximal surface of each axial magnetized magnet 503 is located further along the axis of rotation (towards the proximal end of the rotor) than the proximal surface of each circumferential magnetized magnet 504, and the outer surface of each axial magnetized magnet has an arc length smaller than the arc length of the outer surface of each circumferential magnetized magnet.

Figure 5C:
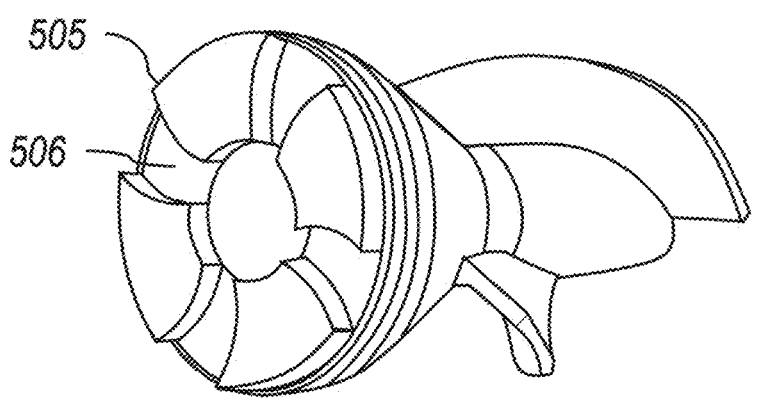

FIG. 5C shows an arrangement of magnets where each magnet has a concave side surface and a convex side surface. The proximal surface of each axial magnetized magnet 505 is located further along the axis of rotation (towards the proximal end of the rotor) than the proximal surface of each circumferential magnetized magnet 506. The outer surface of each axial magnetized magnet has an arc length greater than the arc length of the outer surface of each circumferential magnetized magnet.

In addition, other modifications may be made. For example, in some embodiments, at least one secondary blade is provided on a proximal surface of at least one circumferential magnetized magnet, which extends axially in a proximal direction.

Figure 6A:
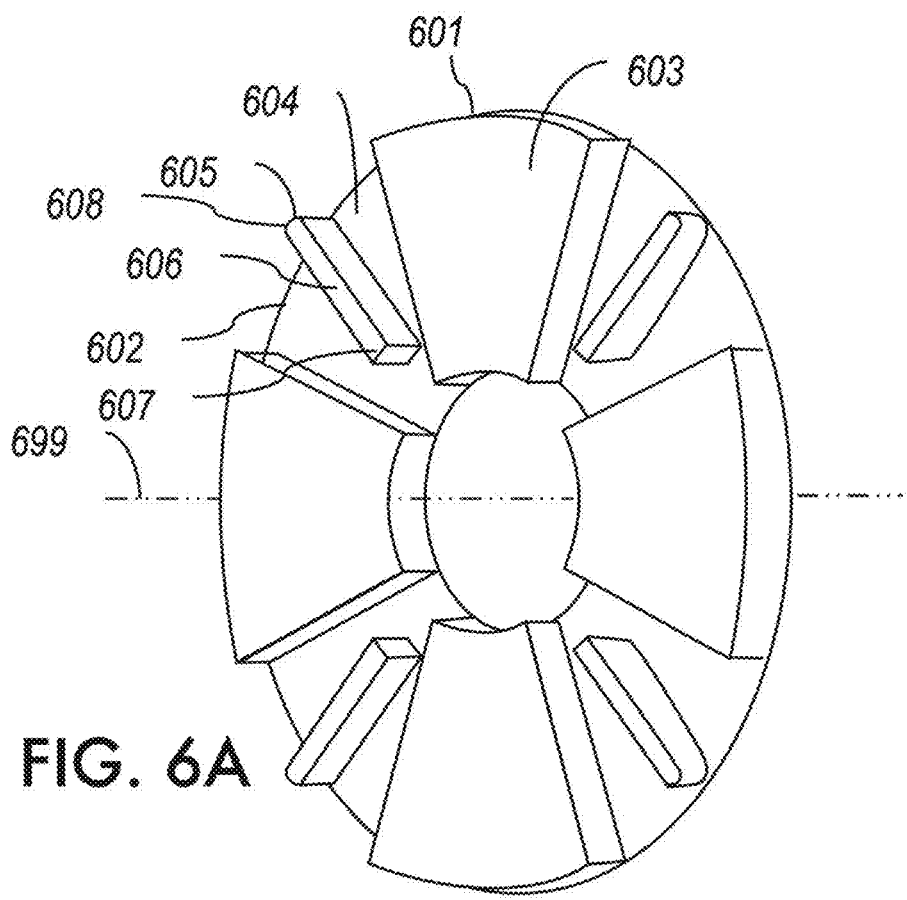
FIG. 6A is a projection view of one embodiment of a modified Halbach array with secondary blades on the circumferential magnetized magnets.

A view of the proximal surfaces of an embodiment of a Halbach array is shown in FIG. 6A. In particular, the modified array includes axial magnetized magnets 601 having a most proximal surface 603 that extend axially further along the axis of rotation 699 in a proximal direction than the most proximal surface 604 of each circumferential magnetized magnet 602. The most proximal surfaces 606 of each blade 605 preferably do not extend beyond the most proximal surfaces 603 of each axial magnetized magnet 601.

The cross-sectional shape of the blade may vary in the radial and/or axial direction. For example, in some embodiments, each blade 605 tapers slightly in the radial direction, as the blade extends away from the axis of rotation 699. In some embodiments, each blade 605 tapers slightly in the axial direction, as the blade extends away from the proximal surface 604 of a circumferential magnetized magnet 602. In some embodiments, the blade tapers in both the radial direction and axial direction. In some embodiments, the proximal surface 606 is angled such that a portion 607 of the proximal surface 606 of the blade 605 that is closest to the axis of rotation is further from the proximal surface 604 of the circumferential magnetized magnet than a portion 608 of the proximal surface 606 of the blade 605 that is further from the axis of rotation 699. Said differently, the height of the blade 605 at a portion 607 close to the axis of rotation 699 is greater than the height of the blade 605 at the portion 608 that is radially further from the axis of rotation.

The general cross-sectional shapes of the blades may vary significantly as desired. For example, while each blade may be generally rectangular, other blades may have curved shapes, trapezoidal or triangular shapes, oval shapes, or even geometric stadium shapes.

In preferred embodiments, each blade has the same shape, but in some embodiments, one or more blades may vary in shape.

Further, in some embodiments, if secondary blades are utilized, the number of secondary blades on each circumferential magnetized magnet is preferably identical. However, in other embodiments, each circumferential magnetized magnet may independently have 0, 1, 2, or 3 blades.

Figures 6B, 6C, 6D:
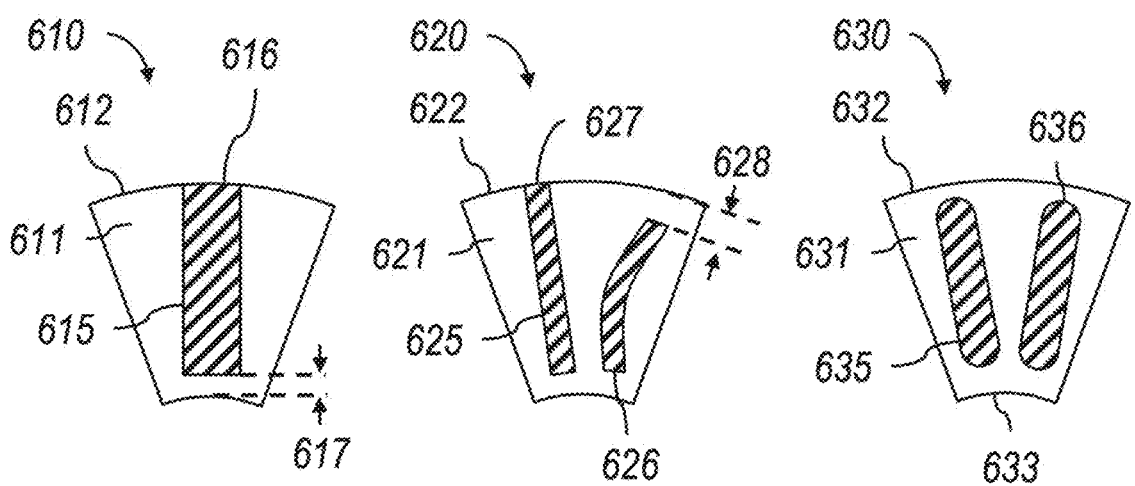
FIGS. 6B-6D show cross-sectional views of alternative embodiments of secondary blades.

FIG. 6B illustrates a cross-sectional view of a circumferential magnetized magnet 610, looking at the proximal surface 611 of the magnet and the secondary blade 615. The shape of the blade is generally rectangular, radially offset from the inner surface of the magnet by a distance 617, and where the outer surface 616 of the blade is substantially flush with the outer surface 612 of the magnet.

It should be recognized that having blades which are radially offset from an inner and/or outer surface of a magnet is not required, although in preferred embodiments, any blades are radially offset from at least the inner surface. When blades are offset from an inner and/or outer surface, any radial offset distance is preferably less than 25% of the radial length of the proximal surface of the magnet, and is typically 1 mm or less.

FIG. 6C illustrates a similar view of the proximal surface 621 of magnet 620. However, here, the magnet has two secondary blades 625, 626, and each is a different shape (in this embodiment, a rectangular blade 625 and an arbitrarily curved blade 626 are illustrated). The rectangular shaped blade 625 has an outer edge or surface that is substantially flush with the outer surface 622 of the magnet 620, but the arbitrarily curved blade 626 is radially offset from the outer surface of the magnet by a distance 628. Both blades are radially offset from the inner surface of the magnet.

FIG. 6D illustrates a similar view of the proximal surface 631 of magnet 630. However, here, the magnet has two identical secondary blades 635, 636, where each secondary blade is a geometric stadium shape. The secondary blades 635, 636 are both offset radially from both the inner and outer surface of magnet 630.

The use of these secondary blades, and the contouring or shaping of the proximal surface of the magnets, may be configured to reduce the axial forces on one or more bearings. As will be understood, more force on a bearing increases the heat generated by the rotation due to, e.g., frictional forces. Beyond increased wear-and-tear on the pump, the heat transfer to blood may lead to further complications. Therefore, in some embodiments, the proximal surface of the magnets are either contoured or contain one or more secondary blades, which may be configured to reduce the axial load on one or more bearings. In some embodiments, there is greater reduction in the load at higher rotational speeds.

Figure 7:
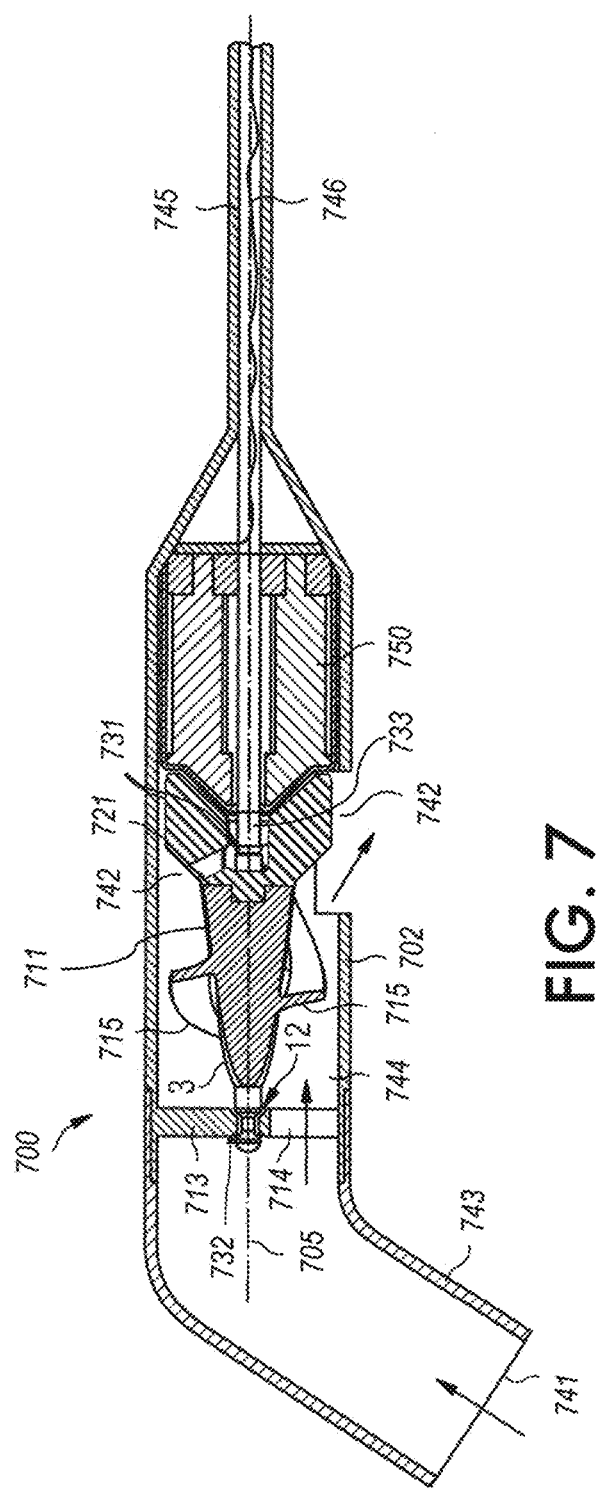
FIG. 7 shows a cross-sectional view of a blood pump according to the present disclosure.

Referring to FIG. 7, a cross-sectional view of a blood pump 700 is illustrated. The blood pump 700 comprises the rotor 711 as described above, and an electric drive unit 750. The blood pump 700 further comprises a pump casing 702 with a blood flow inlet 741 and a blood flow outlet 742. The blood pump 700 is designed as an intravascular pump, also called a catheter pump, and is deployed into a patient's blood vessel by means of a catheter 745. The blood flow inlet 741 is at the end of a flexible cannula 743 which may be placed through a heart valve, such as the aortic valve, during use. The blood flow outlet 742 is located in a side surface of the pump casing 702 and may be placed in a heart vessel, such as the aorta. The blood pump 700 is electrically connected with an electric line 746 extending through the catheter 745 for supplying the blood pump 700 with electric power in order to drive the pump 700 by means of a drive unit 750.

If the blood pump 700 is intended to be used in long term applications, i.e., in situations in which the blood pump 700 is implanted into the patient for several weeks or even months, electric power is preferably supplied by means of a battery. This allows a patient to be mobile because the patient is not connected to a base station by means of cables. The battery can be carried by the patient and may supply electric energy to the blood pump 700, e.g., wirelessly.

The blood is conveyed along a passage 744 connecting the blood flow inlet 741 and the blood flow outlet 742 (blood flow indicated by arrows). Rotor 711 as described above is provided for conveying blood along the passage 744 and is mounted to be rotatable about an axis of rotation 705 within the pump casing 702 by means of a first bearing 731 and a second bearing 732. The axis of rotation 705 is preferably the longitudinal axis of the impeller 711. Both bearings 731, 732 are contact-type bearings in this embodiment. At least one of the bearings 731, 732 could be a non-contact-type bearing, however, such as a magnetic or hydrodynamic bearing. The first bearing 731 is a pivot bearing having spherical bearing surfaces that allow for rotational movement as well as pivoting movement to some degree. A pin 733 is provided, forming one of the bearing surfaces. The second bearing 732 is disposed in a supporting member 713 to stabilize the rotation of the impeller 711, the supporting member 713 having at least one opening 714 for the blood flow. Blades 715 are provided on the rotor 711 for conveying blood once the rotor 711 rotates. Rotation of the rotor 711 is caused by the drive unit 750 which is magnetically coupled to a magnet 731 at the proximal end of rotor 711. The illustrated blood pump 700 is a mixed-type blood pump, with the major direction of flow being axial. It will be appreciated that the blood pump 700 could also be a purely axial blood pump, depending on the arrangement of the rotor 711, and in particular the blades 715.

Skilled artisans will recognize how to configure an electric drive unit to be capable of magnetically interacting with said intravascular blood pump rotor.

to be capable of working with the disclosed rotor. The electric drive unit should be configured to be adjacent to, but physically separated from, the rotor 711. In preferred embodiments, the electric drive unit comprises or consists essentially of a 2-, 4-, or 6-pole stator.

Figure 8A:
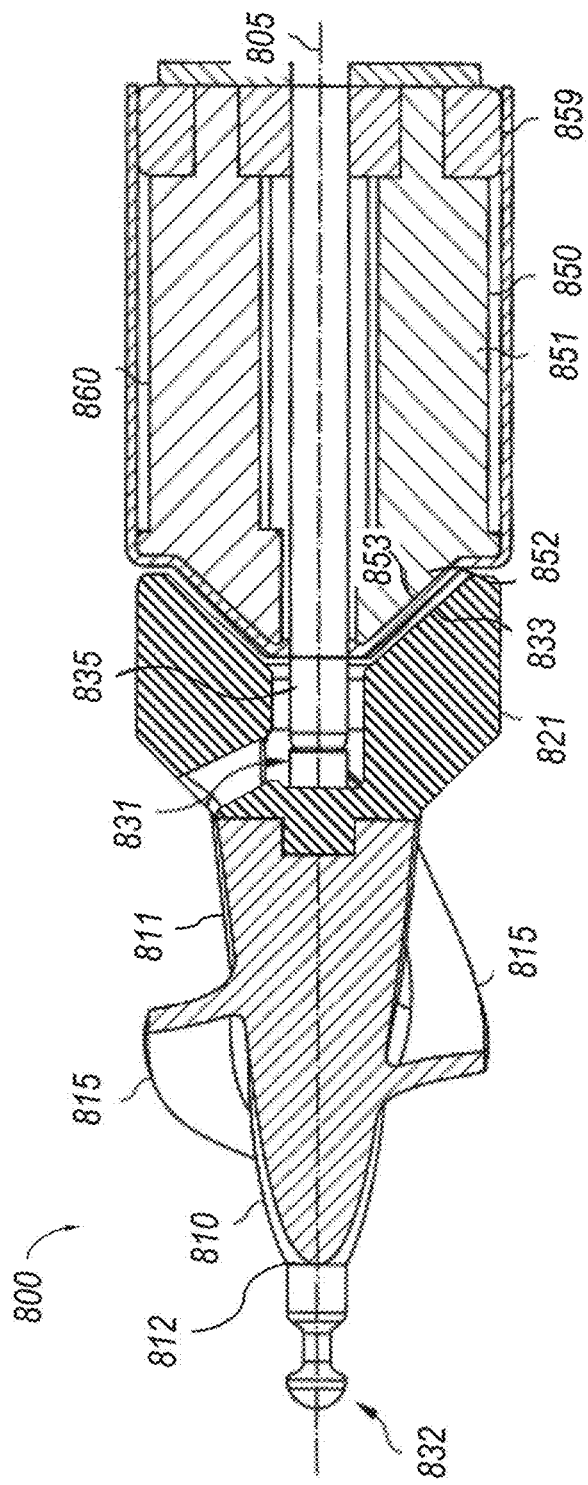
FIG. 8A shows an enlarged detail of the blood pump of FIG. 7.

FIG. 8A illustrates in more detail the interior of one embodiment of the blood pump of FIG. 7. In particular, the interior of the blood pump 801 includes impeller 811 and drive unit 860. In some embodiments, the drive unit 860 comprises a plurality of posts 850, such as six posts 850, only two of which are visible in the cross-sectional view of FIG. 8A. The posts 850 have a shaft portion 851 and a head portion 852. The head portion 852 is disposed adjacent to, but separated from, the rotor 811 in order to magnetically couple the drive unit 860 to the rotor 811. For this purpose, the rotor 811 has a modified Halbach array 821, as described above. The magnets 821 are disposed at the end of the rotor 811 facing the drive unit 860. That is, the magnets 821 are at the proximal end of rotor 811. Due to the shape of the drive unit, the magnets 821 have an inclined proximal surface substantially mirroring the shape of the drive unit.

The posts 850 are sequentially controlled by a control unit (not shown) in order to create a rotating magnetic field for driving the blood pump 800. The magnet 821 is arranged to interact with the rotating magnetic field so as to cause rotation of the rotor 811 about the axis of rotation 805. Coil windings are arranged about the shaft portions 851 of the posts 850. The posts 850 are arranged parallel to the axis of rotation 805, more specifically, a longitudinal axis of each of the posts 850 is parallel to the axis of rotation 805.

In order to close the magnetic flux path, a back plate 859 is typically used. The back plate 859 is located at the end of the shaft portions 851 opposite the head portions 852. The posts 850 act as a magnetic core and are made of a suitable material, in particular a soft magnetic material, such as steel or a suitable alloy, in particular cobalt steel. Likewise, the back plate 859 is made of a suitable soft magnetic material, such as cobalt steel. The back plate 859 enhances the magnetic flux, which allows for reduction of the overall diameter of the blood pump 800, which is important for intravascular blood pumps. Due to the use of the modified Halbach array, no magnetic yoke on the other side of the rotor magnets 821 is required.

Figure 8B:
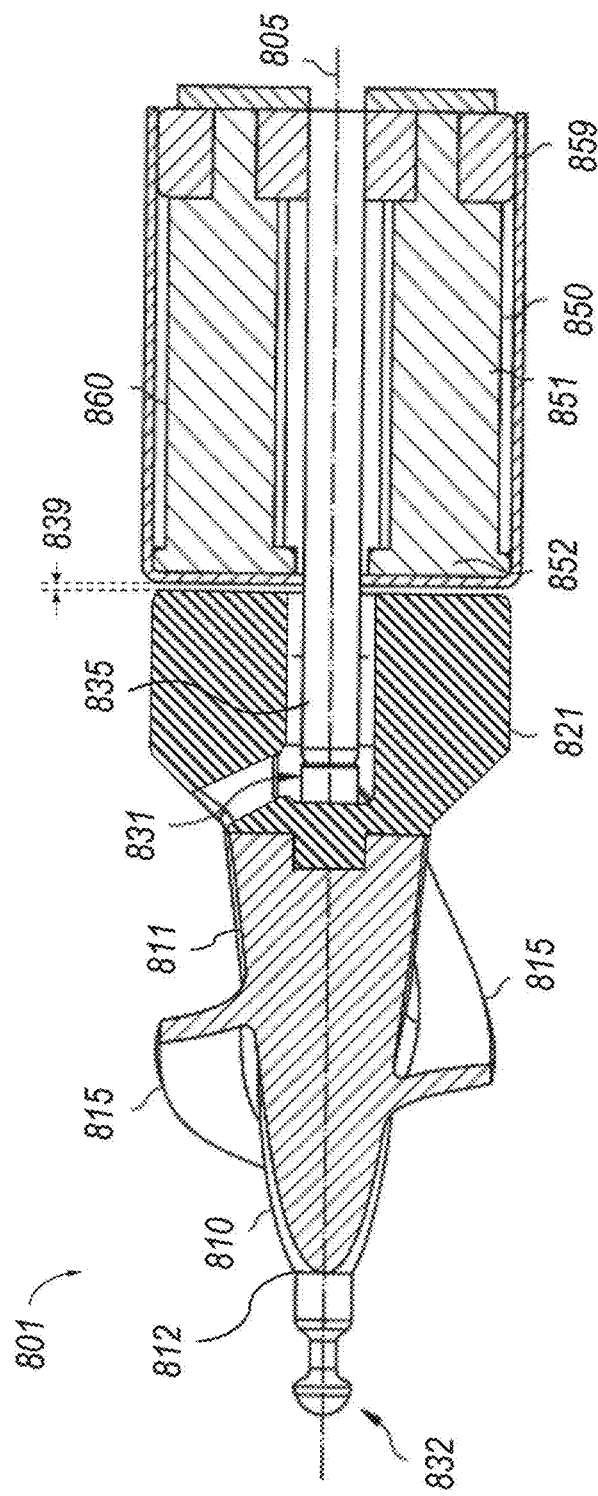
FIG. 8B shows the same view as FIG. 8A according to an alternate embodiment.

FIG. 8B illustrates an alternative embodiment which is substantially similar to the embodiment of FIG. 8A with the exception that top surfaces of the head portions 852 facing the magnets 821 are not inclined but extend in a plane perpendicular to the axis of rotation. Accordingly, the magnets 821 do not have inclined proximal surfaces. The minimum gap 839 between the proximal surfaces of magnets 821 and the distal surface of the drive unit 860 can be easily measured. In some embodiments, the most proximal surface of each circumferential magnetized magnet is further from a distal end of said electric drive unit than the most proximal surface of each axial magnetized magnet.

Those skilled in the art will recognize, or be able to ascertain using no more than routine experimentation, many equivalents to the specific embodiments of the present disclosure described herein. Such equivalents are intended to be encompassed by the following claims.

What is claimed is:

1. An intravascular blood pump rotor, comprising:
a distal portion having a rotor hub tapering in a distal direction and configured to rotate around an axis of rotation, at least one blade extending outward from said rotor hub, and a distal end of said rotor hub extending distally beyond a most distal portion of said at least one blade; and
a proximal portion connected to the distal portion having permanent magnets arranged so as to form a modified Halbach array generating a magnetic field having a first magnetic flux in a proximal direction and a second magnetic flux in a distal direction, said first magnetic flux being greater than said second magnetic flux, said permanent magnets comprising an alternating arrangement of axial magnetized magnets and circumferential magnetized magnets,
wherein at least one of said axial magnetized magnets has a most proximal point or portion of a surface that is a different distance from said distal end as compared to a most proximal point or portion of a surface of at least one of said circumferential magnetized magnets.

2. The intravascular blood pump rotor according to claim 1, wherein the proximal surface of each circumferential magnetized magnet is a first distance axially from said distal end, and the proximal surface of each axial magnetized magnet is a second distance axially from said distal end, said second distance being greater than said first distance.

3. The intravascular blood pump rotor according to claim 2, wherein a difference between said first distance and said second distance is between 1 and 7 mm.

4. The intravascular blood pump rotor according to claim 2, wherein at least two of said proximal surfaces of said circumferential magnetized magnets are not coplanar.

5. An intravascular blood pump, comprising
a pump casing having a blood flow inlet and a blood flow outlet;
an intravascular blood pump rotor according to claim 1; and
an electric drive unit capable of magnetically interacting with said intravascular blood pump rotor.

6. The intravascular blood pump according to claim 5, wherein said electric drive unit comprises a 2-, 4-, or 6-pole stator.

7. The intravascular blood pump according to claim 5, wherein each circumferential magnetized magnet is further from a distal end of said electric drive unit than each axial magnetized magnet.

8. The intravascular blood pump according to claim 5, wherein said intravascular blood pump is an axial flow blood pump.

9. An intravascular blood pump rotor, comprising:
a distal portion having a rotor hub tapering in a distal direction and configured to rotate around an axis of rotation, at least one blade extending outward from said rotor hub, and a distal end of said rotor hub extending distally beyond a most distal portion of said at least one blade; and
a proximal portion connected to the distal portion having permanent magnets arranged so as to form a modified Halbach array generating a magnetic field having a first magnetic flux in a proximal direction and a second magnetic flux in a distal direction, said first magnetic flux being greater than said second magnetic flux, said permanent magnets comprising an alternating arrangement of axial magnetized magnets and circumferential magnetized magnets,
wherein at least one of said axial magnetized magnets has a physical dimension that is different from a corresponding physical dimension of at least one of said circumferential magnetized magnets.

10. The intravascular blood pump rotor according to claim 9, wherein each of said permanent magnets comprises two side surfaces extending radially away from said axis of rotation, said two side surfaces for each of said plurality of permanent magnets forming either two parallel flat surfaces, two non-parallel flat surfaces, or a concave curved surface and a convex curved surface.

11. The intravascular blood pump rotor according to claim 9, wherein said permanent magnets each have an outer surface with a cross-sectional shape forming an arc of a circle about said axis of rotation, an angle subtended by each arc from said axis of rotation being between 1° and 89°.

12. The intravascular blood pump rotor according to claim 11, wherein a first angle subtended by an arc formed by one of said axial magnetized magnets is different than a second angle subtended by an arc formed by one of said circumferential magnetized magnets.

13. The intravascular blood pump rotor according to claim 12, wherein at least one of first or second angles is greater than 45°.

14. The intravascular blood pump rotor according to claim 13, wherein at least one of first or second angles is less than 45°.

15. The intravascular blood pump rotor according to claim 9, wherein said physical dimension comprises a length of an arc formed by a cross-section of an outer surface of each magnet.

16. The intravascular blood pump rotor according to claim 9, wherein said physical dimension comprises a length of each magnet in an axial direction.

17. The intravascular blood pump rotor according to claim 9, wherein said physical dimension comprises a length of an arc formed by a cross-section of an outer surface of each magnet, and a length of each magnet in an axial direction.

18. The intravascular blood pump rotor according to claim 9, further comprising a secondary blade on a proximal surface of at least one circumferential magnetized magnet, extending axially in a proximal direction.

19. An intravascular blood pump, comprising
a pump casing having a blood flow inlet and a blood flow outlet;
an intravascular blood pump rotor according to claim 9; and
an electric drive unit capable of magnetically interacting with said intravascular blood pump rotor.

* * * * *